US006596759B2

(12) United States Patent
Abe et al.

(10) Patent No.: US 6,596,759 B2
(45) Date of Patent: Jul. 22, 2003

(54) MEDICAMENT FOR TREATMENT OF IRRITABLE BOWEL SYNDROME

(75) Inventors: Michikazu Abe, Kanagawa (JP); Ken-Ichi Saito, Kanagawa (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 10/022,274

(22) Filed: Dec. 20, 2001

(65) Prior Publication Data

US 2002/0091152 A1 Jul. 11, 2002

Related U.S. Application Data

(63) Continuation of application No. 09/485,999, filed as application No. PCT/JP98/03665 on Aug. 19, 1998, now abandoned.

(30) Foreign Application Priority Data

Aug. 19, 1997 (JP) ............................................. 9-222424

(51) Int. Cl.[7] ............................................ A61K 31/335
(52) U.S. Cl. ........................ 514/452; 514/456; 514/459
(58) Field of Search ................................. 514/452, 456, 514/459

(56) References Cited

U.S. PATENT DOCUMENTS

| | | | |
|---|---|---|---|
| 4,684,739 A | | 8/1987 | Kikumoto et al. |
| 5,168,099 A | * | 12/1992 | Iwata et al. ................. 514/452 |
| 5,234,948 A | | 8/1993 | Iwata et al. |
| 5,324,738 A | | 6/1994 | Dinan et al. |
| 5,403,848 A | | 4/1995 | Dinan et al. ................. 514/325 |
| 6,160,005 A | | 12/2000 | Shibata et al. |

FOREIGN PATENT DOCUMENTS

| | | |
|---|---|---|
| EP | 0054304 | 6/1982 |
| EP | 419237 | 3/1991 |
| EP | 0446921 | 9/1991 |
| JP | 57108088 | 7/1982 |
| JP | 58219114 | 12/1983 |
| WO | 94/02138 | 2/1994 |
| WO | 96/05817 | 2/1996 |

OTHER PUBLICATIONS

Abe et al., "Reduction of Wrap Restraint Stress–Induced Defecation by MKC–242, a Novel Benzodioxan Derivative, via HT$_{1A}$–Receptor Agonist Action in Rats", Jpn. J. Pharmacol., vol. 77, pp 211–217 (1998).
Miyata et al., "Role of the Serotonin$_3$ Receptor in Stress––Induced Defecation", J. Pharmacol. Exp. Ther., vol. 261, pp 297–303, (1998).
Foreman et al., "Pharmacological Characterization of Enantiomers of 8–Thiomethyl–2–(di–n–propylamino)tetralin, Potent and Selective 5–HT$_{1A}$ Receptor Agonists", Drug Dev. Res., vol. 34, pp 66–85 (1997).

Abe et al., "Novel Benzodioxan Derivative, 5–{3–[((2S)–1, 4–Benzodioxan–2–Ylmethyl)Amino]Propoxy}–1,3–Benzodioxole HCL (MKC–242), with Anxiolytic–Like and Antidepressant–Like Effects in Animal Models", J. Pharmacol. Exp. Ther., vol. 278, pp 898–905 (1996).
Matsuda et al., "Novel Benzodioxan Derivative, 5–{3–[((2S)–1,4–Benzodioxan–2–Ylmethyl)Amino]Propoxy}–1, 3–Benzodioxole HCL (MKC–242), with a Highly Potent and Selective Agonist Activity at Rat Central Serotonin$_{1A}$–Receptors", Jpn. J. Pharmacol., vol. 69, pp 357–366 (1996).
Bobrzynska et al., "Serotonergic Stimulation and Nonphotic Phase–Shifting in Hamsters", Physiology & Behavior, vol. 59, pp 221–230 (1996).
English Language Abstract of JP 57–108088, (1995).
English Language Abstract of JP 58–219114, (1996).
Thompson et al., "Functional Bowel Disorders and Functional Abdominal Pain" (1999) at pp. 43 and 44 of "Rome II: A Multinational Consensus Document on Functional Gastrointestinal Disorders", Gut, vol. 45, Supplement II (Sep. 1999).
Whitehead et al., "Psychologic Considerations in the Irritable Bowel Syndrome" in The Irritable Bowel Syndrome: Realities and Trends Gastroenterology Clinics of North America, vol. 20, No. 2, pp 249–267 (1991).
Friedman, "Treatment of the Irritable Bowel Syndrome" in The Irritable Bowel Syndrome: Realities and Trends, (1999).
Shoichi Asano et al., "Interaction of Orally Administered 5–{3–[((2S)–1,4–Benzodioxan–2–ylmethyl)amino]propoxy}–1,3–benzodioxole (MKC–242) with 5–HT$_{1A}$ Receptors in Rat Brain", Jpn. J. Pharmacol., vol. 74, pp. 69–75 (1997).

(List continued on next page.)

Primary Examiner—Frederick Krass
(74) Attorney, Agent, or Firm—Greenblum & Bernstein, P.L.C.

(57) ABSTRACT

A medicament for preventive and/or therapeutic treatment of irritable bowel syndrome which comprises as an active ingredient a substance selected from the group consisting of an alkylenedioxybenzene derivative represented by the following general formula (I) and a pharmaceutically acceptable salt thereof, and a hydrate thereof and a solvate thereof:

(I)

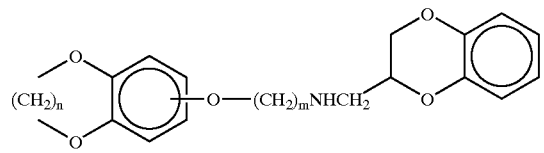

wherein m represents an integer of from 2 to 5, and n represents an integer of from 1 to 3 (e.g., 5-[3-[(2S)-(1,4-benzodioxan-2-ylmethyl)amino]propoxy]-1,3-benzodioxol).

6 Claims, 1 Drawing Sheet

OTHER PUBLICATIONS

Toshio Matsuda et al., "Novel Benzoldioxan Derivates, 5–{3–[((2S)–1,4–Benzodioxan–2–ylmethyl)amino]propoxy}J. –1,3–benzodioxole HCl (MKC–242), with a Highly Potent and Selective Agonish Activity at Rat Central Serotonin$_{1A}$ Receptors", *Jpn. Pharmacol.*, vol. 69, pp. 357–366 (1995).

A. Chua et al., "Central Serotonin Receptors and Delayed Gastric Emptying in Non–Ulcer Dyspepsia", *BMJ*, vol. 305, pp. 280–282 (1992).

R. Berkow et al., The Merck Manual of Diagnosis and Therapy: 59. functional Bowl Disorders, pp. 841–845 (1995).

Lionel Bueno et al., "Mediators and Pharmacology of Visceral Sensitivity: From Basic to Clinical Investigations", *Gastroenterology*, vol. 112, pp. 171–1742 (1997).

* cited by examiner

MEDICAMENT FOR TREATMENT OF IRRITABLE BOWEL SYNDROME

CROSS-REFERENCE TO RELATED APPLICATIONS

This application is a continuation of application Ser. No. 09/485,999, filed Jun. 19, 1998, now abandoned, which was the National Stage of International Application No. PCT/JP98/03665, filed Aug. 19, 1998, which was not published in English under PCT Article 21(2). The entire disclosure of application Ser. No. 09/485,999, now abandoned, is considered as being part of the disclosure of this application, and the entire disclosure of application Ser. No. 09/485,999, now abandoned, is expressly incorporated by reference herein in its entirety. This application is related to Japanese patent application No. 9-222424, filed on Aug. 19, 1997, whose priority is claimed under 35 USC §119, the disclosure of which is incorporated herein by reference in its entirety.

BACKGROUND OF THE INVENTION

1. Field of the Invention

The present invention relates to a medicament useful for therapeutic and/or preventive treatment of irritable bowel syndrome which comprises a particular class of alkylenedioxybenzene derivative as an active ingredient.

2. Discussion of Background Information

Irritable bowel syndrome is caused by factors such as stress, and its main symptoms include somatic symptoms in the digestive system such as abdominal pain and diarrhea. The disease was previously called spastic colon, nervous colitis, mucous colitis, functional colitis, or colonic neurosis. However, the term "bowel" has been used rather than "colon", because the disease is not localized in the large intestine, but the disease is considered as functional disorders of the digestive tract including the small intestine as well. It has been suggested that the disease is caused by physiological factors such as hormones, external stimulations such as food and stress, emotional factors, hereditary body constitutions and the like.

In general, it is difficult to completely eliminate symptoms in the treatment of irritable bowel syndrome. Typically, purposes of therapeutic treatment is to reduce a variety of complaints and to improve conditions so as to be sufficient for daily life. Applicable therapeutic treatments include psychotherapy, life guidance and diet therapy, as well as drug therapy as symptomatic therapy against the patient's complaints (see, references mentioned herein). As drug therapy for irritable bowel syndrome, opioid agonists such as loperamide or anticholinergic agents such as mepenzolate bromide and timepidium bromide have been used to control hypermotility of the digestive tract, and benzodiazepine drugs such as diazepam have been prescribed for anxiety, insomnia and the like. However, no drug therapy that enables causal therapy has been established.

Alkylenedioxybenzene derivatives represented by the following general formula (I) are known:

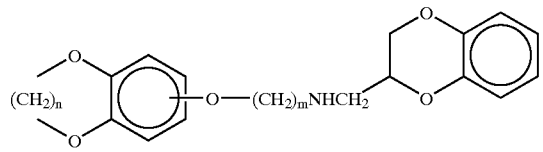

(I)

wherein m represents an integer of from 2 to 5, and n represents an integer of from 1 to 3 (Japanese Patent Unexamined Publication (Kokai) Nos. 3-264528/1991 and 4-288072/1992). These publications disclose that the alkylenedioxybenzene derivatives represented by the general formula bind to a serotonin-1A receptor subtype to exhibit an anti-conflict action, and that the derivatives are useful for therapeutic treatment of anxiety disorders, schizophrenia, circulatory psychosis and the like.

More specifically, affinities (Ki values) for the serotonin 1A receptor subtype are disclosed as for the meta-substituted compound wherein m is 3 and n is 2 (No. 1), the meta-substituted compound wherein m is 3 and n is 2 (No. 2), the meta-substituted compound wherein m is 3 and n is 3 (No. 3), the meta-substituted compound wherein m is 4 and n is 1 (No. 4), the meta-substituted compound wherein m is 4 and n is 3 (No. 6), the meta-substituted compound wherein m is 5 and n is 1 (No. 7), and the ortho-substituted compound wherein m is 3 and n is 1 (No. 13). These patent documents also disclose that the compounds of Nos. 1 to 3 have an anti-conflict action, and are useful for the treatment of anxiety disorders, schizophrenia, manic-depressive illness and the like.

Serotonin was revealed to participate in the regulation of intestinal motility, and effectiveness of serotonin-3 receptor subtype antagonists in inhibition of the intestinal motility has been suggested (Miyata et. al., J. Pharmacol. Exp. Ther., 261, pp.297–303, 1992). Serotonin-1A receptor subtype agonists are also known to inhibit rat defecation induced by the load of forced swimming stress (Foreman et. al., Drug Dev. Res., 34, pp.66–85, 1995). However, although the forced swimming test has been established as a screening method for antidepressants, its adequacy as an animal model for irritable bowel syndrome has not yet been clarified. Further, tandospirone, one of the serotonin-1A receptor agonists, revealed to have improving effect on patients with irritable bowel syndrome in a double-blind test, but failed to give a significant difference in therapeutic efficacy compared with a placebo (Kimura et. al., Clinical Evaluation (Rinsho Hyoka), 20, pp.225–257, 1992). Japanese Patent Unexamined Publication (Kokai) Nos. 3-264528/1991 and 4-288072/1992 neither suggest nor teach that the aforementioned compounds have therapeutic efficacy for irritable bowel syndrome.

SUMMARY OF THE INVENTION

The present invention provides a medicament useful for preventive and/or therapeutic treatment of irritable bowel syndrome. The inventors of the present invention found that a particular class of alkylenedioxybenzene derivatives were effective in a pathologic model of irritable bowel syndrome and useful for preventive and/or therapeutic treatment of irritable bowel syndrome. The present invention was achieved on the basis of the above findings.

The present invention thus provides a medicament for preventive and/or therapeutic treatment of irritable bowel syndrome which comprises as an active ingredient a substance selected from the group consisting of alkylenedioxy-benzene derivatives represented by the following general formula (I) and pharmaceutically acceptable salts thereof, and hydrates thereof and solvates thereof:

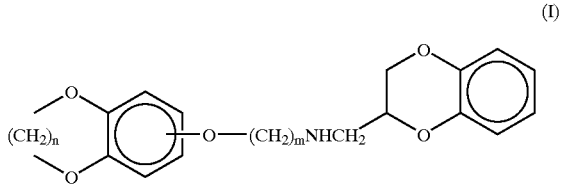

(I)

wherein m represents an integer of from 2 to 5, and n represents an integer of from 1 to 3. As a preferred embodiment of the aforementioned medicament of the present invention, there is provided a medicament for preventive and/or therapeutic treatment of irritable bowel syndrome, which comprises as an active ingredient a substance selected from the group consisting of alkylenedioxybenzene derivatives represented by the aforementioned general formula (I) wherein n is 1 (most preferably 5-[3 [(2S)-(1,4-benzodioxan-2-ylmethyl)amino]propoxy]-1,3-benzodioxol) and physiologically acceptable salts thereof, and hydrates thereof and solvates thereof.

According to another preferred embodiment, the aforementioned medicament for preventive and/or therapeutic treatment is provided as a pharmaceutical composition comprising a substance selected from the aforementioned group as an active ingredient together with a pharmaceutical additive.

From other aspects, there are provided use of a substance selected from the group consisting of the alkylenedioxybenzene derivatives represented by the aforementioned general formula (I) and pharmaceutically acceptable salts thereof, and hydrates thereof and solvates thereof for the manufacture of the aforementioned medicament for preventive and/or therapeutic treatment of irritable bowel syndrome; and a method for preventive and/or therapeutic treatment of irritable bowel syndrome, which comprises the step of administering to a mammal including a human an effective amount of a substance selected from the group consisting of the alkylenedioxybenzene derivatives represented by the aforementioned general formula (I) and pharmaceutically acceptable salts thereof, and hydrates thereof and solvates thereof.

BRIEF DESCRIPTION OF THE DRAWINGS

FIG. 1(a) shows that the action of the medicament of the present invention is inhibited by N-tert-butyl-3-(4-(2-methoxyphenyl)-piperazin-1-yl)-2-phenyl-propanamide (WAY 100135) which is a serotonin 1A receptor antagonist. FIG. 1(b) shows that the action of the medicament of the present invention is inhibited by 1-(2-pyrimidinyl)piperazine (1-PP) which is a common metabolite of buspirone and tandospirone as control drugs. In the figure, * indicates that significant difference was observed at a significance level of 5% in the one-way analysis of variance (ANOVA) and followed by the Tukey's (multiple comparison) test.

DETAILED DESCRIPTION OF THE PRESENT INVENTION

Figure 1:
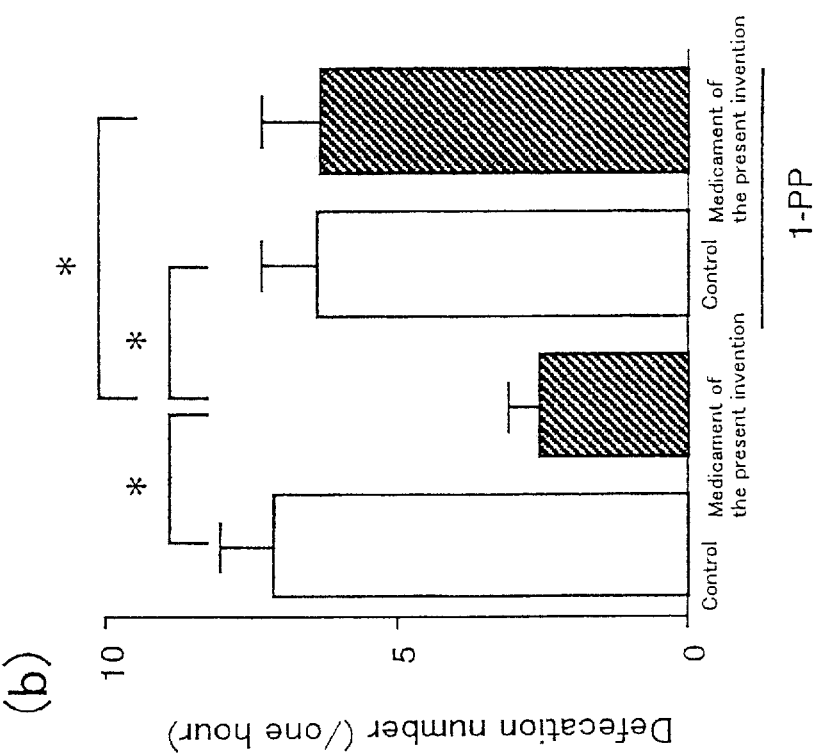
FIG. 1 shows the effect of drugs that inhibit the action of the medicament of the present invention.
Figure 1:
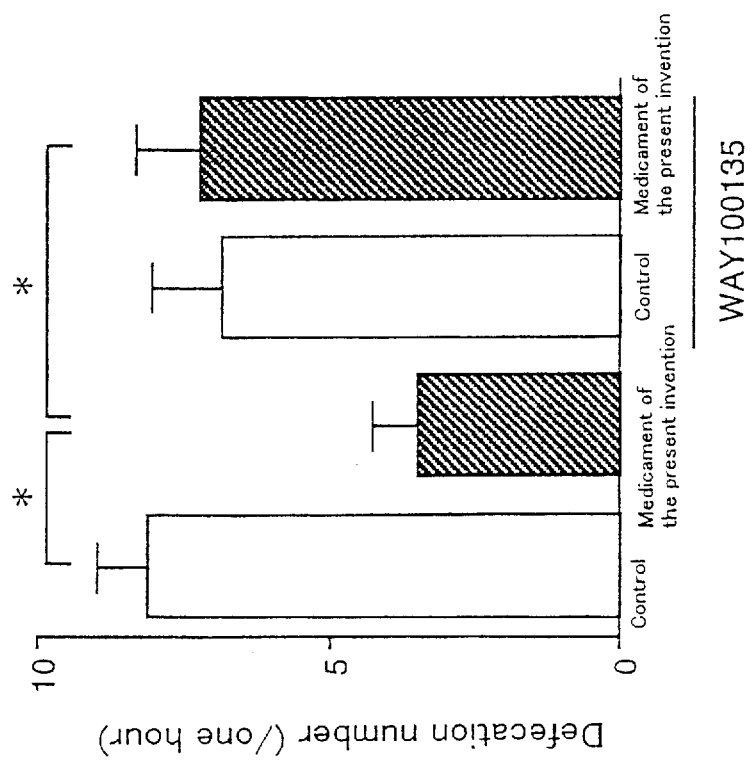

The medicament of the present invention for the preventive and/or therapeutic treatment comprises as an active ingredient a substance selected from the group consisting of the alkylenedioxybenzene derivatives represented by the aforementioned general formula (I) and pharmaceutically acceptable salts thereof, and hydrates thereof and solvates thereof. The alkylenedioxybenzene derivatives represented by the general formula (I) are known, and their methods of preparation are disclosed in Japanese Patent Unexamined Publication (Kokai) Nos. 57-108088/1982, 58-219114/1983 and 3-264528/1991. Therefore, these substances are readily obtained by those skilled in the art. Among the alkylenedioxybenzene derivatives represented by the aforementioned general formula (I), those wherein n is 1 are preferred. A position of the aminoalkyleneoxy group on the phenyl ring may be either at the ortho-position or the meta-position relative to one of the oxygen atoms of the alkylenedioxy group. The meta-position is preferred.

As the active ingredient of the medicament of the present invention, the alkylenedioxybenzene derivatives represented by the general formula (I) in free forms as well as physiologically acceptable salts thereof may be used. Examples of such salts include mineral acid salts such as hydrochlorides, phosphates and sulfates, and organic acid salts such as acetates, formates, citrates and p-toluenesulfonates. Furthermore, any hydrate or solvate of the compound in a free form or a salt thereof may also be used as the active ingredient of the medicament of the present invention. Solvents that can constitute the solvates are not particularly limited so long as they- are physiologically acceptable, and examples include methanol, ethanol, isopropanol, acetone, ethyl acetate and the like. Among them, ethanol solvates and the like may preferably be used.

The alkylenedioxybenzene derivatives represented by the general formula (I) have one asymmetrical carbon, and two optical isomers thereof exist. Preparing methods of these optical isomers and medicinal applications thereof are described in Japanese Patent Unexamined Publication (Kokai) No. 4-288072/1992, and the two optical isomers are applicable to those skilled in the art. As the active ingredient of the medicament of the present invention, any one of optical isomers in an optical pure form or any mixture of optical isomers may be used. When optical isomers are used, those in S-configuration are preferred. A racemate which is a mixture of equal amounts of optical isomers may also be used.

Examples of the alkylenedioxybenzene derivatives preferred as the active ingredient of the medicament of the present invention are shown below. However, the active ingredients of the medicament of the present invention are not limited to the following derivatives.

TABLE 1

| Compound No. | m | n |
|---|---|---|
| 1 | 3 | 1 |
| 2 | 3 | 2 |
| 3 | 3 | 3 |
| 4 | 4 | 1 |
| 5 | 4 | 2 |
| 6 | 4 | 3 |
| 7 | 5 | 1 |
| 8 | 5 | 2 |
| 9 | 5 | 3 |

TABLE 1-continued (structure: alkylenedioxybenzene with O(CH₂)ₘNHCH₂ linker to benzodioxane)

| Compound No. | m | n |
|---|---|---|
| 10 | 2 | 1 |
| 11 | 2 | 2 |
| 12 | 2 | 3 |

TABLE 2

(structure: alkylenedioxybenzene with O—(CH₂)ₘNHCH₂ linker to benzodioxane)

| Compound No. | m | n |
|---|---|---|
| 13 | 3 | 1 |
| 14 | 3 | 2 |
| 15 | 3 | 3 |
| 16 | 4 | 1 |
| 17 | 4 | 2 |
| 18 | 4 | 3 |
| 19 | 5 | 1 |
| 20 | 5 | 2 |
| 21 | 5 | 3 |
| 22 | 2 | 1 |
| 23 | 2 | 2 |
| 24 | 2 | 3 |

Among the compounds exemplified in the aforementioned Tables 1 and 2, a particularly preferred compound includes Compound No. 1. This compound is specifically described in Japanese Patent Unexamined Publication (Kokai) Nos. 3-264528/1991 and 4-288072/1992. Japanese Patent Unexamined Publication (Kokai) Nos. 3-264528/1991 and 4-288072/1992 disclose that the alkylenedioxybenzene derivatives of the formula (I) as the active ingredient according to the present invention have high affinity for a serotonin 1A receptor subtype, and have an anti-conflict action. These publications also disclose that the alkylenedioxybenzene derivatives are useful for the treatment of anxiety disorders, schizophrenia, manic-depressive illness and the like. However, the publications neither suggest nor teach that those derivatives are useful for the treatment of irritable bowel syndrome.

The medicament of the present invention is useful for preventive and/or therapeutic treatment of irritable bowel syndrome. Irritable bowel syndrome is defined as a functional disease of the intestinal tract wherein in general constipation, diarrhea, alternating defecation abnormality and the like are continued with various indefinite abdominal complaints, whist any organic pathological changes to which the symptoms are attributable are not verified in internal and external parts of the intestinal tract and related organs (Matsunaga et al., Irritable Bowel Syndrome, Ed. by Masuda, M.; Lecture of Clinical Digestive Diseases 2, Intestinal Diseases, Kinbara Shuppan, 1977). The disease may also be referred to as spastic colon, nervous colitis, mucous colitis, functional colitis or colonic neurosis. The disease may sometimes include diseases that have been called as sigma elongatum mobile, cecum mobile, chronic colitis, splanchnoptosia and the like. Typological classification of the disease generally include convulsive large bowel, diarrhea nervosa and colica mucosa, and the disease may also be classified in convulsive constipation type, chronic diarrhea type, atonic constipation type, intestinal gas syndrome, or chronic celiopathy.

Furthermore, irritable bowel syndrome may also include cholangiodyskinesia, gastric emptying hypofunction, hysteric globus, non-specific esophagus functional abnormalities, nervous vomiting, recurrent abdominal pain, simple constipation and the like. Therefore, the term "irritable bowel syndrome" used in the specification should be construed in its broadest sense so as to include these diseases. As diagnostic criteria of irritable bowel syndrome, those of NIH, Manning, Cook et al. and the like have been proposed. It should be understood that skilled physicians can readily diagnose the disease according to any one of these criteria, and suitably decide the use of the medicament of the present invention (as a review of irritable bowel syndrome, see, Asakura, H., "Stress and Irritable Bowel Syndrome", Clinical Digestive Internal Medicine, Vol. 8, No. 8, pp.1373–1381, 1993).

As the medicament of the present invention, a substance, per se, that is selected from the group consisting of the alkylenedioxybenzene derivative and a pharmaceutically acceptable salt thereof, and a hydrate thereof and a solvate thereof may be administered to a mammal including human. However, it is generally preferable to prepare a pharmaceutical composition comprising one or more of the aforementioned substances as an active ingredient and one or more of pharmaceutical additives and administer the composition to a patient. Examples of the pharmaceutical composition include, for example, formulations for oral administration such as tablets, capsules, subtilized granules, powders, pills, troches, sublingual tablets and liquid preparations, and formulations for parenteral administration such as injections, drip infusions, suppositories, transdermal preparations, transmucosal preparations, inhalants and patches for transdermal absorption and the like.

Tablets and capsules for oral administration are usually provided in a unit dosage form, and can be prepared by using ordinary pharmaceutical additives such as binders, fillers, diluents, compressing agents, lubricants, disintegrating agents, coloring matters, flavoring agents and moistening agents. Tablets may be coated according to a method well known in the art, for example, by using an enteric coating agent, and they may also be prepared by using fillers such as cellulose, mannitol and lactose; disintegrating agents such as starch, polyvinylpyrolidone, starch derivatives and sodium starchglycolate; lubricants such as magnesium stearate; moistening agents such as sodium laurylsulfate and the like.

Liquid preparations for oral administration can be provided in the forms of, for example, aqueous or oily suspensions, solutions, emulsions, syrups and elixirs, as well as dried formulations such as lyophilized preparations that can be dissolved before use by addition of water or a suitable aqueous medium. Those liquid preparations may contain ordinary pharmaceutical additives, for example, suspending agents such as sorbitol, syrups, methylcellulose, gelatin, hydroxyethylcellulose, carboxymethylcellulose, aluminum stearate gel and hydrogenated edible fats; emulsifiers such as lecitin, sorbitan monooleate and gum arabic; non-aqueous media including edible oils such as almond oil, rectified coconut oil, oily esters (e.g., esters of glycerin), propylene glycol and ethyl alcohol; preservatives such as methyl ester, ethyl ester and propyl ester of p-hydroxybenzoic acid and sorbic acid; and usual flavoring agents and coloring matters as required.

Formulations for oral administration can be manufactured according to a method well known in the art, for example, by mixing, filling, compressing and the like. In addition, it is also possible to disperse the active ingredient in a formulation containing a large amount of filler by repetitive mixing. Formulations for parenteral administration such as injections and drip infusions are generally provided as unit dosage form preparations containing the aforementioned substance as the active ingredient and a sterilized medium. Such formulations can be prepared by dissolving the aforementioned substance in a suitable medium, subjecting the resulting solution to filtration for sterilization, filling the solution in vials or ampoules, and sealing the vials or ampoules. It is also possible to freeze the composition and fill the result in vials, and then eliminate the moisture in vacuo to improve stability. Suspensions for parenteral administration can be prepared by substantially the same method as that applied to solutions for parenteral administration; however, the suspensions can preferably be manufactured by suspending the active ingredient in a medium, and then subjecting the result to gas sterilization using ethylene oxide or the like. Furthermore, surface active agents, moistening agents and so forth may also be added so that a uniform dispersion of the active ingredient can be obtained.

Doses of the medicament of the present invention can be suitably decided depending on the purpose of administration, i.e., therapeutic or preventive treatment, nature of a disease to be treated or prevented, conditions, body weight, age, sexuality and the like of a patient. In an usual case, an amount of about 0.01 mg to 1,000 mg, preferably about 1 to 100 mg per day for an adult as the amount of the active ingredient may be administered orally. Such doses may be administered once a day to several times a day as divided portions.

EXAMPLE

The present invention will be explained more specifically with reference to example 1. However, the scope of the present invention is not limited to the following example 1. In the example, Compound No. 1 shown in the above Table 1 (m=3; n=1; and meta-substituted, referred to as the "medicament of the present invention" hereinafter in examples) was used as the active ingredient of the medicament of the present invention.

Example 1

Action of the Medicament of the Present Invention on the Animal Model of Irritable Bowel Syndrome Increase of defecation number induced by restraint stress has widely been used as a pathological model of irritable bowel syndrome (Miyata et al., J. Pharmacol. Exp. Ther., 261, pp.297–303, 1992). Therefore, pathological model animals of irritable bowel syndrome were prepared according to the method of Williams et al. (Williams et al., Gastroenterology, 94, pp.611–621, 1988) and used for evaluation of the effectiveness of the medicament of the present invention. The medicament of the present invention was administered to the rats, and after 1 hour, their forelegs were fixed on their trunks with adhesive tapes under ether anesthesia (load of restraint stress). One hour after the restraint, defecation number was counted and the number was compared with that of the control group. In the experiments using a combination of drugs, the medicament of the present invention was administered to the animals 30 minutes before the restraint, and the other drug was administered 1 hour before the restraint. Due to the load of the restraint stress, the defecation number of the rats significantly increased from 0.2 to 11.5 pieces in average. The medicament of the present invention dose-dependently suppressed the increase of defecation number induced by the restraint (Table 3).

When 8-hydroxy-2-(di-n-propylamino)tetralin (8-OH-DPAT) as a serotonin 1A receptor agonist was intraperitoneally administered, the defecation due to the stress was suppressed as in the case of the administration of the medicament of the present invention. However, other serotonin 1A receptor agonists, i.e., buspirone and tandospirone, failed to exhibit significant efficacy (Table 3). Furthermore, amitriptyline as an antidepressant and diazepam as an anxiolytic agent exhibited significant suppressive actions at a high dose (100 mg/kg and 30 mg/kg, respectively), but they exhibited no efficacy at a lower dose (Table 3). These results indicate that the defecation suppressing activity is not commonly observed in every serotonin 1A receptor agonist, and that antidepressants and anxiolytic agents are generally almost ineffective in the treatment of irritable bowel syndrome.

The action of the medicament of the present invention was inhibited by N-tert-butyl-3-(4-(2-methoxyphenyl) piperazin-1-yl)-2-phenyl-propanamide (WAY100135) as a serotonin 1A receptor antagonist (FIG. 1($a$)). Furthermore, the action was antagonized by 1-(2-pyrimidinyl)piperazine (1-PP), which is a common metabolite of the control drugs, buspirone and tandospirone (FIG. 1($b$)). These results suggest that the action of the medicament of the present invention was mediated by the serotonin 1A receptor.

It has been reported that a serotonin 1A agonist has an activity for suppressing defecation induced by forced swimming stress in rats (Foreman et al., Drug Dev. Res., 34, pp.66–85, 1995). According to the report, buspirone also exhibited significant defecation suppressing activity. Therefore, the forced swimming stress model described in the publication may possibly be different from the restraint stress model (that was used in the test example), which has been established as a pathological model of irritable bowel syndrome, and the forced swimming stress model may be unsuitable as a pathological model of irritable bowel syndrome. In addition, anxiolytic activity of the medicament of the present invention was observed in an animal model (Abe et al., J. Pharmacol. Exp. Ther., 278, pp.898–905, 1996). Therefore, in the treatment of irritable bowel syndrome, the medicament of the present invention is considered to directly control the motile function of the intestinal tract, and synergistically enhance the therapeutic efficacy by eliminating anxiety.

TABLE 3

| Compound (Administration route) | Dose (mg/kg) | Suppression rate of defecation number (%) |
| --- | --- | --- |
| Drug of the present invention (oral) | 0.3 | 29 |
| | 1 | 45* |
| | 3 | 81* |
| Buspirone (oral) | 10 | 12 |
| | 30 | 12 |
| | 100 | 44 |
| Tandospirone (oral) | 30 | 8 |
| | 100 | 4 |
| | 300 | 44 |

TABLE 3-continued

| Compound (Administration route) | Dose (mg/kg) | Suppression rate of defecation number (%) |
|---|---|---|
| Diazepam (oral) | 3 | 26 |
|  | 10 | 36 |
|  | 30 | 77* |
| Amitriptyline (oral) | 10 | 17 |
|  | 30 | 6 |
|  | 100 | 69* |
| Fluoxetin (oral) | 10 | 24 |
|  | 30 | 15 |
|  | 100 | 26 |
| 8-OH-DPAT (intraperitoneal) | 0.03 | 25 |
|  | 0.1 | 74* |
|  | 0.3 | 97* |

*Significant difference at a significance level of 5%

INDUSTRIAL APPLICABILITY

The medicament of the present invention is useful for preventive and/or therapeutic treatment of irritable bowel syndrome.

What is claimed is:

1. A method for the prophylactic treatment of irritable bowel syndrome comprising administering to a mammal in need thereof an effective amount for the prophylactic treatment of irritable bowel syndrome of at least one of an alkylenedioxybenzene derivative, a pharmaceutically acceptable salt thereof, a hydrate thereof or a solvate thereof, the alkylenedioxybenzene derivative being represented by the formula:

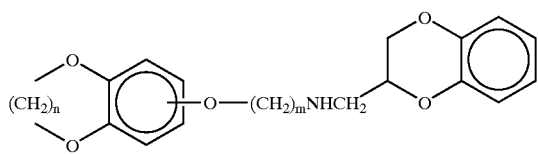

(I)

wherein m represents an integer from 2 to 5, and n represents an integer from 1 to 3.

2. The method for the prophylactic treatment of irritable bowel syndrome of claim 1 wherein n is 1.

3. The method for the prophylactic treatment of irritable bowel syndrome of claim 2 wherein the alkylenedioxybenzene derivative is 5-[3-[(2S)-(1,4-benzo-dioxan-2-ylmethyl)amino]propoxyl]-1,3-benzodioxol.

4. A method for the therapeutic treatment of irritable bowel syndrome comprising administering to a mammal in need thereof an effective amount for the therapeutic treatment of irritable bowel syndrome of at least one of an alkylenedioxybenzene derivative, a pharmaceutically acceptable salt thereof, a hydrate thereof or a solvate thereof, the alkylenedioxybenzene derivative being represented by the formula:

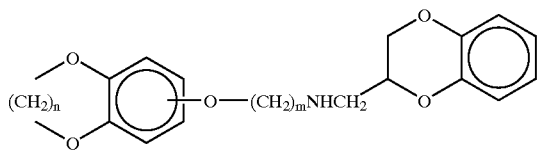

(I)

wherein m represents an integer from 2 to 5, and n represents an integer from 1 to 3.

5. The method for the therapeutic treatment of irritable bowel syndrome of claim 4 wherein n is 1.

6. The method for the therapeutic treatment of irritable bowel syndrome of claim 5 wherein the alkylenedioxybenzene derivative is 5-[3-[(2S)-(1,4-benzo-dioxan-2-ylmethyl)amino]propoxyl]-1,3-benzodioxol.

* * * * *